United States Patent [19]

Harper et al.

[11] Patent Number: 4,900,673
[45] Date of Patent: Feb. 13, 1990

[54] MUTANT HUMAN ANGIOGENIN (ANGIOGENESIS FACTOR WITH SUPERIOR ANGIOGENIN ACTIVITY) GENES THEREFOR AND METHODS OF EXPRESSION

[75] Inventors: Jeffrey W. Harper, Newton Highlands; Bert L. Vallee, Brookline, both of Mass.

[73] Assignee: President and Fellows of Harvard College, Boston, Mass.

[21] Appl. No.: 173,760

[22] Filed: Mar. 28, 1988

[51] Int. Cl.$^4$ .................. C12N 15/00; C12N 9/22; C12N 1/20; C07H 15/12
[52] U.S. Cl. .................. 435/199; 435/172.3; 435/240.2; 435/252.3; 435/252.33; 435/320; 536/27; 935/14; 424/94.61
[58] Field of Search .................. 536/27; 435/68, 70, 435/170, 172.1, 172.3, 199, 252.3, 252.33, 240.2; 530/351; 935/10, 11, 12, 13, 14, 22, 23, 44, 55, 66, 82

[56] References Cited

U.S. PATENT DOCUMENTS 4,721,672 1/1988 Vallee .................. 435/70

Primary Examiner—Thomas G. Wiseman
Assistant Examiner—Anne Brown
Attorney, Agent, or Firm—Allegretti & Witcoff, Ltd.

[57] ABSTRACT

Site-specific mutagenesis of a gene for angiogenin producing DNA sequences encoding mutant proteins having increased angiogenic activity are disclosed. Expression vectors containing these sequences are introduced into host cells and direct the production of the mutant angiogenic proteins with markedly increased angiogenic and ribonucleolytic activity. Replacement of a single amino acid, the aspartic acid at position 116 of human angiogenin, with another amino acid including asparagine, alanine or histidine, yields mutant proteins with 8 to 15 fold increased ribonucleolytic activity toward tRNA and rRNA and 10 to 100 fold increased angiogenic potency in the chorioallantoic membrane assay. The mutant angiogenin proteins of this invention are useful therapeutic compositions to promote the development of a hemovascular network in a mammal or to promote wound healing, in particular, healing of torn or traumatized fibrocartilage material.

9 Claims, 5 Drawing Sheets

```
    -1  1                                                    15
    Met<Glu-Asp-Asn-Ser-Arg-Tyr-Thr-His-Phe-Leu-Thr-Gln-His-Tyr-Asp-
                                                             30
    Ala-Lys-Pro-Gln-Gly-Arg-Asp-Asp-Arg-Tyr-Cys-Glu-Ser-Ile-Met-
                                                             45
    Arg-Arg-Arg-Gly-Leu-Thr-Ser-Pro-Cys-Lys-Asp-Ile-Asn-Thr-Phe-
                                                             60
    Ile-His-Gly-Asn-Lys-Arg-Ser-Ile-Lys-Ala-Ile-Cys-Glu-Asn-Lys-
                                                             75
    Asn-Gly-Asn-Pro-His-Arg-Glu-Asn-Leu-Arg-Ile-Ser-Lys-Ser-Ser-
                                                             90
    Phe-Gln-Val-Thr-Thr-Cys-Lys-Leu-His-Gly-Gly-Ser-Pro-Trp-Pro-
                                                             105
    Pro-Cys-Gln-Tyr-Arg-Ala-Thr-Ala-Gly-Phe-Arg-Asn-Val-Val-Val-
                                            116              120
    Ala-Cys-Glu-Asn-Gly-Leu-Pro-Val-His-Leu-Asp-Gln-Ser-Ile-Phe-
             123                                   -(Asn)-
    Arg-Arg-Pro-OH.                                -(Ala)-
                                                   -(His)-
```

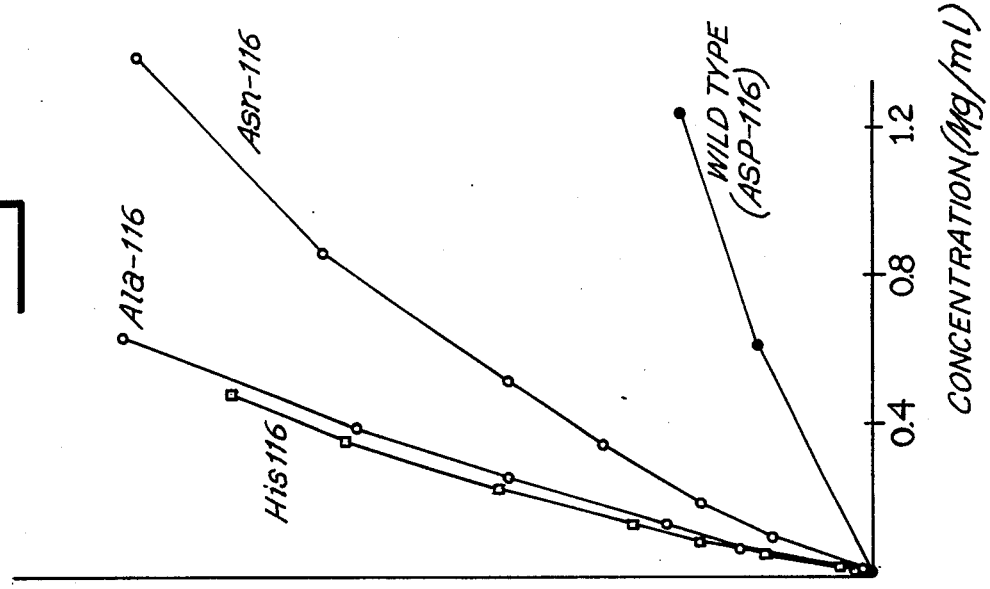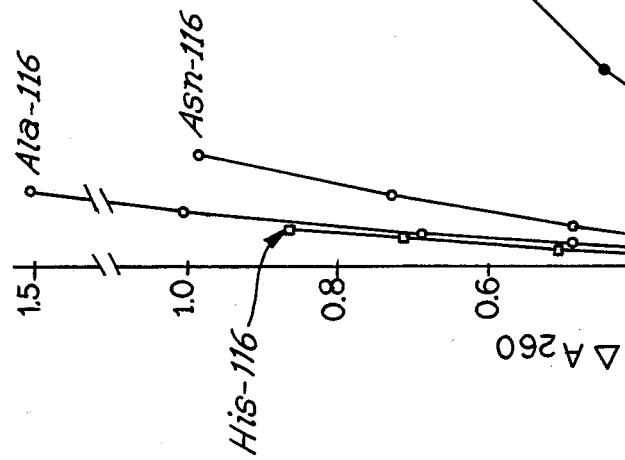

Fig. 4

```
                        KpnI
                        ┌──┐CTAATTTACCAACACTACTACGTTTTAA
                        ├──┤----------+---------+--------+
                        └──┘CATGGATTAAATGGTTGTGATGATGCAAAATT
```

```
CTGAAACAAACTGGAGACTGCCATGCAGGACAACTCGAGGTATACACATTTCCTGACCCA
---------+---------+---------+---------+---------+---------+
GACTTTGTTTGACCTCTGACGGTACGTCCTGTTGAGCTCCATATGTGTAAAGGACTGGGT
                                                           12
              Met GlnAspAsnSerArgTyr ThrHisPheLeuThrGln
                 <──────────────────><────────────────
                         T-1                 T-7
```

```
GCACTATGACGCTAAACCGCAGGGCGGGGACGATCGTTACTGCGAATCGATTCTGAGACG
---------+---------+---------+---------+---------+---------+
CGTGATACTGCGATTTGGCGTCCCGGCCCTGCTAGCAATGACGCTTAGCTAAGACTCTGC
                                                     30     32
  HisTyrAspAlaLysProGlnGlyArgAspAspArgTyrCysGluSerIleLeuArgArg
 ──────────────────><────────────────────────> Met**  <─────
         T-9                    T-9'                    T-13
```

```
CCGTGGGTTAACTAGTCCGTGCAAAGATATCAACACTTTCATCCATGGTAACAAGCGTTC
---------+---------+---------+---------+---------+---------+
GGCACCCAATTGATCAGGCACGTTTCTATAGTTGTGAAAGTAGGTACCATTGTTCGCAAG
                                                          52
  ArgGlyLeuThrSerProCysLysAspIleAsnThrPheIleHisGlyAsnLysArgSer
  ─────><──────────────────><──────────────────────────><
          T-10'                        T-8
```

```
TATCAAAGCCATATGCGAAAACAAAAACGGTAACCCGCATCGCGAAAACCTGCGCATCAG
---------+---------+---------+---------+---------+---------+
ATAGTTTCGGTATACGCTTTTGTTTTTGCCATTGGGCGTAGCGCTTTTGGACGCGTAGTC
                                                          72
  IleLysAlaIleCysGluAsnLysAsnGlyAsnProHisArg GluAsnLeuArgIleSer
  ──────><──────────><──────────────><──────><──────────><
  T-3a    T-11'          T-4a           T-5       T-3b
```

```
CAAGTCAAGCTTCCAGGTTACAACTTGCAAACTTCATGGGGGATCCCCGTGGCCGCCATG
---------+---------+---------+---------+---------+---------+
GTTCAGTTCGAAGGTCCAATGTTGAACGTTTGAAGTACCCCCTAGGGGCACCGGCGGTAC
                                                          92
  LysSerSerPheGlnValThrThrCysLysLeuHisGlyGlySerProTrpProProCys
  ──────────────────><──────────────────────><
           T-9"                    T-10"
```

```
CCAGTACCGTGCTACTGCCGGCTTCCGTAATGTTGTGGTTGCTTGTGAAAACGGTCTGCC
---------+---------+---------+---------+---------+---------+
GGTCATGGCACGATGACGGCCGAAGGCATTACAACACCAACGAACACTTTTGCCAGACGG
                                                          112
  GlnTyrArgAlaThrAlaGlyPheArgAsnValValAlaCysGluAsnGlyLeuPro
  ──────────><──────────────><
      T-6                T-11"
                                EcoRI
```

```
AGTCCATCTAGATCAGTCTATCTTCCGAAGGCCTTAATAG┌──┐
---------+---------+---------+---------+├──┤
TCAGGTAGATCTAGTCAGATAGAAGGCTTCCGGAATTATC└──┘    *pHA1
     116             123                       **pHA2
  ValHisLeuAspGlnSerIlePheArgArgProEndEnd
  ──────────────────><
          T-11"        T-2"
```

Fig. 5

```
        -1   1                                              15
        Met<Glu-Asp-Asn-Ser-Arg-Tyr-Thr-His-Phe-Leu-Thr-Gln-His-Tyr-Asp-
                                                                     30
        Ala-Lys-Pro-Gln-Gly-Arg-Asp-Asp-Arg-Tyr-Cys-Glu-Ser-Ile-Met-
                                                                 45
        Arg-Arg-Arg-Gly-Leu-Thr-Ser-Pro-Cys-Lys-Asp-Ile-Asn-Thr-Phe-
                                                                 60
        Ile-His-Gly-Asn-Lys-Arg-Ser-Ile-Lys-Ala-Ile-Cys-Glu-Asn-Lys-
                                                                 75
        Asn-Gly-Asn-Pro-His-Arg-Glu-Asn-Leu-Arg-Ile-Ser-Lys-Ser-Ser-
                                                                 90
        Phe-Gln-Val-Thr-Thr-Cys-Lys-Leu-His-Gly-Gly-Ser-Pro-Trp-Pro-
                                                                 105
        Pro-Cys-Gln-Tyr-Arg-Ala-Thr-Ala-Gly-Phe-Arg-Asn-Val-Val-Val-
                                                         116     120
        Ala-Cys-Glu-Asn-Gly-Leu-Pro-Val-His-Leu-Asp-Gln-Ser-Ile-Phe-
        123                                              -(Asn)-
                                                         -(Ala)-
        Arg-Arg-Pro-OH.                                  -(His)-
```

MUTANT HUMAN ANGIOGENIN (ANGIOGENESIS FACTOR WITH SUPERIOR ANGIOGENIN ACTIVITY) GENES THEREFOR AND METHODS OF EXPRESSION

BACKGROUND OF THE INVENTION

1. Field of the Invention

This invention relates to mutant angiogenin genes produced by site-specific mutagenesis and recombinant DNA techniques and includes DNA sequences for the mutant angiogenic genes which encode mutant proteins with increased angiogenic and ribonucleolytic activities. Additionally, the invention relates to methods of expression of mutant angiogenic proteins with increased angiogenic and ribonucleolytic activities as well as the resulting mutant angiogenic proteins.

It has now been unexpectedly found that replacement of the aspartic acid at or corresponding to position 116 (Asp-116) of human angiogenin with another amino acid, in particular, asparagine (Asn), alanine (Ala), or histidine (His), by site-specific mutagenesis of an angiogenin gene, results in a significant enhancement of both the angiogenin and ribonucleolytic activity of angiogenin.

2. Background of the Art

Angiogensis, the process of developing a hemovascular network, is essential for the growth of solid tumors and is a component of normal wound healing and growth processes. It has also been implicated in the pathophysiology of atherogenesis, arthritis, and diabetic retinopathy. It is characterized by the directed growth of new capillaries toward a specific stimulus. This growth, mediated by the migration of endothelial cells, may proceed independently of endothelial cell mitosis.

The molecular messengers responsible for the process of angiogenesis have long been sought. Greenblatt and Shubik (J. Natl. Cancer Inst. 41: 111-124, 1968) concluded that tumor-induced neovascularization is mediated by a diffusible substance. Subsequently, a variety of soluble mediators have been implicated in the induction of neovascularization. These include prostaglandins (Auerback, in *Lymphokines,* Pick and Landy, eds., 69-88, Academic Press, New York, 1981), human urokinase (Berman et al., Invest. Opthalm. Vis. Sci. 22; 191-199, 1982), copper (Raju et al., J. Natl. Cancer Inst. 69: 1183-1188, 1982), and various "angiogenesis factors."

Angiogenesis factors have been derived from tumor cells, wound fluid (Banda et al., Proc. Natl. Acad. Sci. USA 79: 7773-7777, 1982; Banda et al., U.S. Pat. No. 4,503,038), and retinal cells (D'Amore, Proc. Natl. Acad. Sci. USA 78: 3068-3072, 1981). Tumor-derived angiogenesis factors have in general been poorly characterized. Folkman et al. (J. Exp. Med. 133: 275-288, 1971) isolated tumor angiogenesis factor from the Walker 256 rat ascites tumor. The factor was mitogenic for capillary endothelial cells and was inactivated by ribonuclease (RNase). Tuan et al. (Biochemistry 12: 3159-3165, 1973) found mitogenic and angiogenic activity in the nonhistone proteins of the Walker 256 tumor. The active fraction was a mixture of proteins and carbohydrate. A variety of animal and human tumors have been shown to produce angiogenesis factor(s) (Phillips and Kuman, Int. J. Cancer 23: 82-88, 1979) but the chemical nature of the factor(s) was not determined. A low molecular weight non-protein component from Walker 256 tumors has been shown to be angiogenic and mitogenic (Weiss et al., Br. J. Cancer 40: 493-496, 1979). An angiogenesis factor with a molecular weight of 400-800 daltons was purified to homogeneity by Fenselau et al. (J. Biol. Chem. 256: 9605-9611, 1981), but it was not further characterized. Human lung tumor cells have been shown to secrete an angiogenesis factor comprising a high molecular weight carrier and a low molecular weight, possibly non-protein, active component (Kumar et al., Int. J. Cancer 32: 461-464, 1983). Vallee et al. (Experientia 41: 1-15, 1985) found angiogenic activity associated with three fractions from Walker 256 tumors. Tolbert et al. (U.S. Pat. No. 4,229,531) disclose the production of angiogenesis factor from the human adenocarcinoma cell line HT-29, but the material was only partially purified and was not chemically characterized. Isolation of genes responsible for the production of the above described angiogenesis factors has not been reported at least in part due to the lack of purity and characterization of the factors.

Isolation of angiogenesis factors has employed high performance liquid chromatography (Banda et al., ibid); solvent extraction (Folkman et al., ibid); chromatography on silica gel (Fenselau et al., ibid); DEAE cellulose (Weiss et al., ibid), or Sephadex Tuan et al, ibid); and affinity chromatography (Weiss et al., ibid).

Recently, Vallee et al. (U.S. Pat. No. 4,727,137 which is hereby incorporated by reference) have purified an angiogenic protein from a human adenocarcinoma cell line. The protein has been identified in normal human plasma (Shapiro, et al. Biochem. 26: 5141-5146, 1987). The purified protein, known as angiogenin, was chemically characterized and its amino acid sequence determined. Two distinct, although apparently linked, biological activities have been demonstrated for the human tumor-derived angiogenin. First, it was reported to behave as a very potent angiogenic factor in vivo (Fett et al., Biochem. 24: 5480-5456, 1985). Second, it has been found to exhibit a characteristic ribonucleolytic activity (Shapiro et al., Biochem. 25: 3527-3532, 1986).

In addition, Vallee et al. (U.S. Pat. No. 4,721,672, which is hereby incorporated by reference) recently have cloned the gene (both cDNA and genomic) encoding the angiogenic protein from the human adenocarcinoma cell line described and claimed in the above referenced U.S. Pat. No. 4,727,137. They have cloned the gene in vectors and have transformed or transfected host cells with recombinant vectors encoding the angiogenin gene. Such transformed or transfected cells express a human angiogenin protein.

Denèfle et al. (Gene 56: 61-70, 1987), have prepared a synthetic gene coding for human angiogenin. The gene was designed to use codons found in highly expressed *E. coli* proteins and was ligated into a pBR322-derived expression vector constructed to contain the *E. coli* tryptophan (trp) promoter. This *E. coli*-produced angiogenin was found to be insoluble but could be easily renatured and purified. The purified angiogenin exhibited angiogenic activity and ribonucleolytic activity similar to that described for natural angiogenin purified by Vallee et al. (U.S. Pat. No. 4,727,137) from human adenocarcinoma cells.

Hoechst (German Patent Application P3716722.7) has prepared a different synthetic gene for angiogenin with a leucine at position 30 instead of the methionine at position 30 in the natural angiogenin gene described by Vallee et al. (U.S. Pat. No. 4,721,672). In addition, this synthetic gene was designed to use codons preferentially expressed in *E. coli.* The gene was subcloned into a vector containing a modified trp promoter (European Patent Application 0198415) and a translation initiation region (TIR) sequence (Gene 41: 201–206, 1986; EMBO J. 4: 519–526, 1985) to increase translation efficiency. The synthetic gene is under direct control of the trp promoter and expression is induced by addition of indole-3-acrylic acid or by tryptophan starvation. The leu-30 angiogenin protein could be purified and was found to exhibit angiogenic and ribonucleolytic activity similar to that of natural angiogenin.

All the angiogenin proteins just described, whether plasma-derived, tumor cell-derived or recombinant DNA-derived (cDNA, genomic DNA or synthetic gene derived) exhibit both angiogenic activity and ribonucleolytic activity. These two activities have not yet been separated. Indeed, one of the most intriguing features of angiogenin is its structural homology with mammalian pancreatic ribonucleases (RNases). Overall, there is a 35% sequence identity between human pancreatic RNase and angiogenin (Strydom et al., Biochemistry 24: 5486–5494, 1985). This structural relationship should permit the study of the mechanism of action of angiogenin, as well as the relationship between the angiogenic and enzymatic (ribonucleolytic) activities of angiogenin.

Because angiogenesis factors play an important role in wound healing (Rettura et al. FASEB Abstract #4309, 61st Annual Meeting, Chicago, 1977) and may find applicability in the development of screening tests for malignancies (Klagsburn et al., Cancer Res. 36: 110–114, 1976; Brem et al. Science 195: 880–881, 1977), it is clearly advantageous to produce angiogenic proteins in sufficient quantities to permit their application in therapy and diagonsis. The techniques of genetic engineering are ideally suited to increase production levels of these proteins. The cloning of genes encoding angiogenic proteins, such as described in U.S. Pat. No. 4,721,672, is a necessary first step in such a large-scale production. In addition to increasing production levels of angiogenic proteins, it would be highly advantageous to use cloned genes to produce mutant or variant angiogenic proteins with angiogenic activity that is much increased over wild-type activity. The techniques of site-specific mutagenesis and genetic engineering are ideally suited to producing proteins with such increased activity. Although it is clear that the amino acids of an angiogenic protein may be modified by such techniques to produce proteins with altered biological activities, it is difficult to predict which amino acids should be altered and whether such an alteration will increase or decrease biological activity. U.S. Pat. No. 4,721,672 states that the cysteines at positions 26, 39, 57, 81, 92 and 107, and histidines at positions 13 and 114, and the lysine at position 40 should be preferred sites for replacement by other amino acids using site-specific mutagenesis.

Furthermore, it may in some instances be desirable to obtain these mutant angiogenic proteins with increased angiogenic activity from non-tumor cells, such as in the case of human therapeutics, where contamination with certain tumor products would be unacceptable and where an increase in biological activity could permit the use of lower dosage levels. This invention therefore provides for the production of mutant angiogenic proteins in non-tumor cells with increased angiogenic activity using site-specific mutagenesis and recombinant DNA techniques.

SUMMARY OF THE INVENTION

It has now been unexpectedly found that replacement of aspartic acid at or corresponding to position 116 of human angiogenin by another amino acid, specifically by Asn, Ala or His, using site-specific mutagenesis of an angiogenin gene, results in 8 to 15 fold enhancement of ribonucleolytic activity toward tRNA or rRNA and 10 to 100 fold enhancement in angiogenic potency. Briefly stated, the present invention discloses mutant or variant DNA sequences encoding mutant angiogenin proteins having superior angiogenic activity. A DNA sequence encoding a mutant angiogenin, or a mutant angiogenin protein having substantially the same type of biological activity as angiogenin, but with higher activity than that of non-mutated or wild-type angiogenin, is also disclosed. The DNA sequences may be obtained by site-specific mutagenesis of a DNA sequence encoding angiogenin (wild-type DNA sequence). The wild-type sequence suitable for mutagenesis may be any DNA segment encoding angiogenin, and may be cDNA, genomic DNA or may be a synthetic gene.

The invention further discloses vectors comprising a mutant or variant DNA sequence encoding a mutant or variant protein having superior angiogenic activity. Vectors comprising a DNA sequence encoding a protein having substantially the same, but increased biological activity as non-mutant or wild-type angiogenin are also disclosed. The vectors further comprise a promoter sequence upstream of and operably linked to the DNA sequence. In general, the vectors will also contain a selectable marker, and, depending on the host cell used, may contain such elements as regulatory sequences, polyadenylation signals, enhancers, and RNA splice sites.

An additional aspect of the present invention discloses cells transfected or transformed to produce a mutant protein having superior angiogenic activity. Cells transferred or transformed to produce a mutant or variant protein having substantially the same, but increased biological activity as non-mutant or wild-type angiogenin are also disclosed. The cells are transfected or transformed to contain an expression vector comprising a DNA sequence encoding a mutant or variant protein having superior angiogenic activity. While expression of the gene encoding for the 116 mutant angiogenin protein is illustrated in bacteria, expression in yeast and mammalian cells is performed by art-recognized techniques and is contemplated by this invention.

A further aspect of the present invention discloses a method for producing a mutant or variant protein having superior angiogenic activity. The method comprises (a) obtaining a mutant or variant angiogenin gene by site-specific mutagenesis of a non-mutant or wild-type angiogenin gene; (b) introducing into a host cell a vector comprising a DNA sequence encoding a mutant or variant protein having angiogenic activity; (c) growing the host cell in an appropriate medium; and (d) isolating the mutant or variant protein product encoded by the DNA sequence and produced by the host cell. A method for producing a mutant or variant protein having substantially the same but substantially increased biological activity as angiogenin is also disclosed. The mutant proteins produced by these methods are also disclosed. In addition, portions of the human angiogenin proteins having the aspartic acid corresponding to Asp-116 altered are likewise encompassed by the present invention. It has been discovered that mutating the aspartic acid in the region corresponding to amino acids at or corresponding to 112 through 121 of wild-type angiogenin (Pro-Val-His-Leu-Asp-Gln-Ser-Ile-Phe-Arg) increases the angiogenin activity of the resultant mutant angiogenin protein or a biologically active peptide fragment thereof.

Other aspects of the invention will become evident upon reference to the detailed description and drawings.

BRIEF DESCRIPTION OF THE DRAWINGS

FIG. 3 is a graph of the ribonucleolytic activity of wild-type angiogenin and the Asp-116 mutants of angiogenin with tRNA as substrate.

FIG. 4 illustrates the DNA sequence coding for angiogenin in pHA1 and pHA2. The amino acid sequence is also shown. Solid lines with arrows indicate the position and numbers of the tryptic peptides analyzed.

FIG. 5 illustrates the amino acid sequence of wild-type angiogenin and mutations at or corresponding to position 116. Bacterially expressed angiogenin has a methionine (met) at position -1.

DETAILED DESCRIPTION

Figure 1:
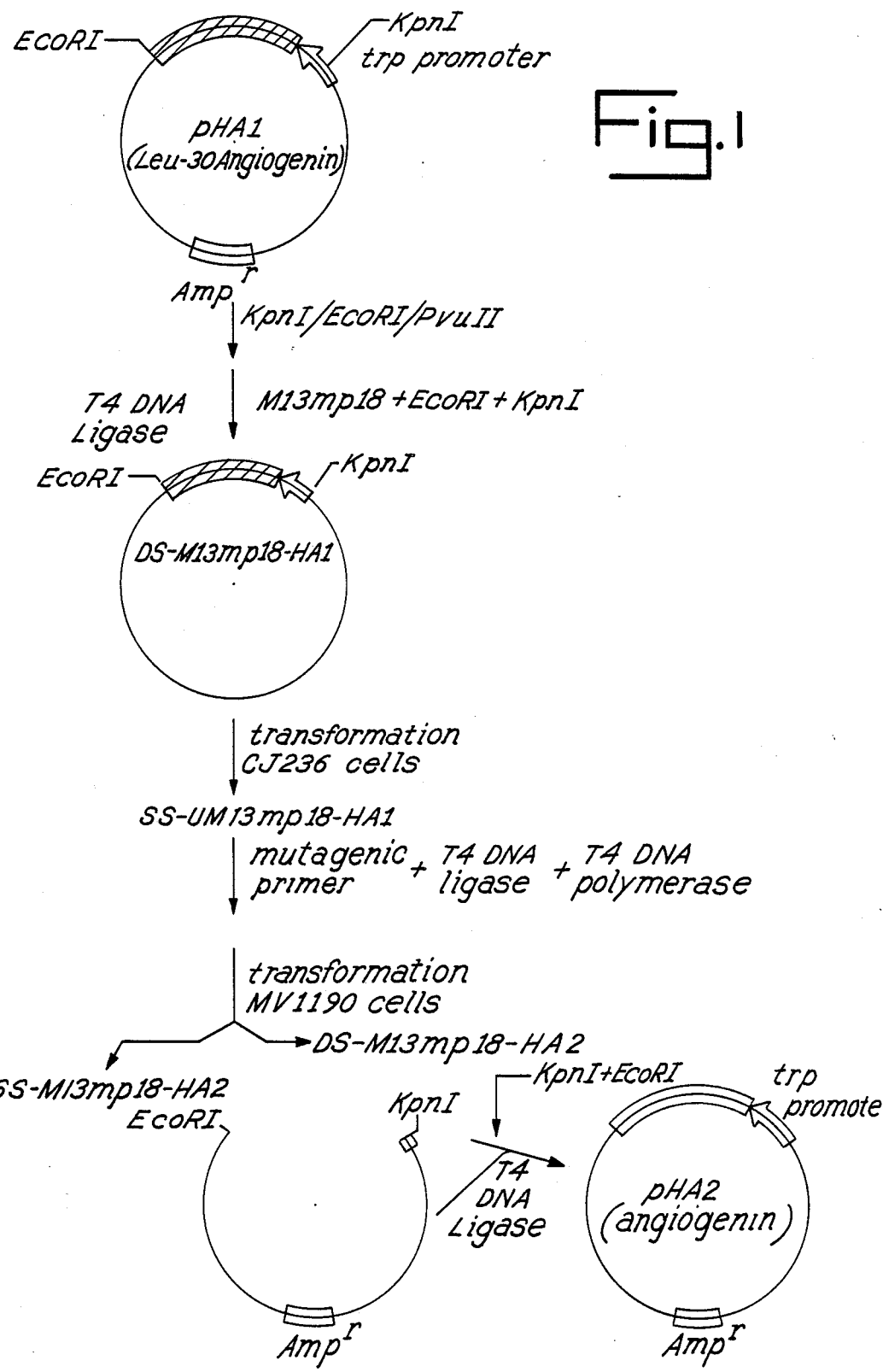
FIG. 1 illustrates the construction of the pHA2 expression vector for angiogenin.

Prior to setting forth the invention, it may be helpful to define certain terms to be used hereinafter.

Biological activity is a function or set of functions performed by a molecule in a biological context (i.e., in an organism or an in vitro facsimile). For angiogenin, biological activity is characterized by its angiogenic activity. It may also include ribonucleolytic activity.

Angiogenic activity is the chemical stimulation of hemovascular development in tissue. It is generally associated with diffusible substances produced by a variety of cell types. Angiogenic activity may be characterized by a positive response in the chick embryo chorioallantoic membrane assay (Knighton et al., Br. J. Cancer 35: 347-356, 1977) and/or the rabbit cornea implant assay (Langer and Folkman, Nature 263: 797-800, 1976).

Ribonucleolytic activity is the ribonuclease (RNase) enzymatic activity associated with angiogenin, in particular, catalytic activity with certain RNA substrates, including the limited catalysis or cleavage of rRNA and tRNA.

A mutant gene is a DNA molecule, or a clone of such a molecule, which has been modified by human intervention to contain segments of DNA which are changed, combined or juxtaposed in a manner which would not otherwise exist in nature.

A mutant angiogenin protein is an angiogenin protein or any peptide fragment of that protein in which one or more amino acids have been replaced with other amino acids, and which has altered biological activity when compared with non-mutated or wild-type angiogenin.

Angiogenic proteins are produced by a variety of cell types, including tumor cells and retinal cells. Until recently, these proteins have not been obtained in sufficient purity to permit their chemical and physical characterization. A variety of techniques and procedures discussed in detail in U.S. Pat. No. 4,721,672, which is incorporated by reference, with respect to the isolation and assay of angiogenic proteins and with respect to the cloning and expression of angiogenic genes, including various vector systems and host cell systems, would apply equally to the mutant angiogenic genes and proteins of the present invention. For example, mutant angiogenin proteins of this invention can be produced in host cells such as bacteria, yeast and mammalian cells which have been transformed or transfected with a mutant DNA segment to express the mutant angiogenin protein. In addition to techniques and procedures described in U.S. Pat. No. 4,721,672, those skilled in the art will recognize other suitable techniques and procedures.

Amino acids of an angiogenic protein may be replaced by other amino acids by site-specific mutagenesis (Zoller et al., Manual for Advanced Techniques in Molecular Cloning Course, Cold Spring Harbor Laboratory, 1983). Thus, site-specific mutagenesis can be used to replace one or more amino acids in wild-type angiogenin and the resultant mutated DNA sequence will encode a mutant angiogenic protein that will have substantially the same amino acid sequence as wild-type angiogenin, but may have an altered (reduced or increased) biological activity. A mutant angiogenin having reduced or no angiogenic activity, but retaining certain structural features, may still bind receptors on endothelial or other cells and thus form an antagonist to the action of the wild-type angiogenin by blocking the cell receptor. Such mutants may be useful in the treatment of angiogenesis-related disease states. The methods described herein can be applied to obtain such mutants.

Mutant angiogenins that exhibit higher levels of biological activity than wild-type angiogenin may also be obtained by site-specific mutagenesis. Increased biological activity could permit the use of lower dosage levels of such high-activity mutant angiogenin proteins. The methods described herein have been successfully applied to obtain such mutants.

Because of the homology between angiogenin and ribonuclease, certain amino acids have been suggested to be preferred sites for replacement by site specific mutagenesis: the cysteines at positions 26, 39, 57, 81, 92 and 107, the histidines at positions 13 and 114, and the lysine at position 40. (Vallee et al. U.S. Pat. No. 4,721,672). None of these suggested sites were selected for the generation of the mutant angiogenins of the present invention, however, any of these suggested amino acids or other amino acid can be selected and replaced by site-specific mutagenesis of an angiogenin gene. In the preferred embodiment of this invention, the aspartic acid at position 116 was the selected site for mutagenesis. Replacement of this residue with another amino acid by site-specific mutagenesis, in particular, asparagine, alanine or histidine, unexpectedly results in a marked enhancement of both the angiogenic and the ribonucleolytic activity of angiogenin.

Mutant angiogenic proteins produced according to the present invention may be used to produce therapeutic or diagnostic compositions by combining them with suitable carriers. The therapeutic compositions may be used to promote the development of a hemovascular network in a mammal, for example, to induce collateral circulation following a heart attack, or to promote wound healing, for example, in joints or other locations. Preferably, the therapeutic compositions according to the present invention of a mutant angiogenin protein in a non-toxic pharmaceutically acceptable carrier will be administered intravenously or by direct topical application to the wound site. For example, if injury occurs to the meniscus of the knee or shoulder as frequently occurs in sports-related injuries or osteoarthritis, implantation or injection of angiogenic proteins at the site of the injury may promote healing of torn or traumatized fibrocartilage material. Effective doses will vary according to the severity of the condition and the target tissue. Furthermore, angiogenic proteins have diagnostic applications in screening for the presence of malignancies, either by using the protein to assay for the presence of antibodies or to produce antibodies for use as immunodiagnostic reagents. A diagnostic composition containing the protein may be incubated with a biological sample under conditions suitable for the formation of an antigen-antibody complex. The formation of the complex (i.e., the presence of antibodies in the sample) is then detected. Techniques for such assays are well known in the art, e.g. the enzyme linked immunosorbent assay (Voller et al., *The Enzyme Linked Immunasorbent Assay*, Dynatech Laboratories, Inc. (1979) or the Western blot assay (see, for example, Towbin et al. *Proc. Natl Acad Sci. USA* 76, 4350, 1979). Similarly, a diagnostic composition comprising an antibody against an angiogenic protein may be used to assay for the presence of the protein in a biological sample. The angiogenic proteins may also be used to develop angiogenesis inhibitors which may be useful in the treatment of disorders associated with angiogenesis. Recombinant DNA and site-specific mutagenesis provide superior methods for the production of these proteins in the quantities needed and with increased biological activity for therapeutic applications.

EXPERIMENTAL

Materials and Methods

Restriction endonucleases, T4 DNA ligase, T4 kinase, M13mp18 (RF) were from Bethesda Research Laboratory, New England Biolabs, or International Biotechnologies, Inc. Oligonucleotide-directed or site-specific mutagenesis was by the method of Kunkel, Proc. Natl. Acad. Sci. USA 82: 488–492, 1985, employing the Muta-Gene TM in vitro mutagenesis kit from BioRad Laboratories. [$\alpha^{35}$S] dATP was from New England Nuclear. *E. coli* strain W3110 cells (A.T.C.C. 27325) were provided by Hoechst A.G. JM101 cells were obtained from Pharmacia or Bethesda Research Laboratory.

Small-scale plasmid DNA preparations were performed using the alkaline lysis method described by Maniatis et al., *Molecular Cloning, A Laboratory Manual*, Cold Spring Harbor Laboratory, 1982. Single-stranded and double-stranded M13 DNA were prepared using procedures described in the New England Biolabs M13 cloning and sequencing manual. Cultures of JM101 cells (2 ml) were grown to an O.D.$_{600}$ of approximately 0.1–0.2, an M13 plaque added and the phage propagated for 6 hours at 37° C. with shaking. Cells were collected by centrifugation and used to prepare double-stranded M13 DNA using the alkaline lysis method. Phage were obtained from supernatants by precipitation with 1/5 volume of 2.5M NaCl in 20% polyethylene glycol (6000), resuspended in 10 mM Tris-HCl, pH 8.0 with 1.0 mM ethylenediamine tetraacetic acid (TE), and DNA obtained by sequential extractions with phenol, phenol/chloroform, and chloroform (2x). DNA was precipitated with 3M ammonium acetate and 2 volumes of ethanol and dissolved in TE buffer. The single-stranded DNA was quantitated by using agarose gel electrophoresis and staining with ethidium bromide employing standards of known concentration.

DNA sequencing with modified T7 DNA polymerase was carried out by the chain termination method of Sanger et al., Proc. Natl. Acad. Sci. USA 74: 5463–5467 (1977) using a Sequenase TM kit obtained from United States Biochemical in combination with [$\alpha$-$^{35}$S]ATP. Phosphorylation of oligonucleotides (400 pmol) was accomplished with T4 kinase (9 U) in 100 mM Tris, pH 8, 5 mM DTT, 10 mM MgCl$_2$, and 0.43 mM ATP. Incubations were carried out for 45 min at 37° followed by 10 min at 65° C.

EXAMPLE 1

Preparation of *E. coli* Expression Vector Recombinant Human Angiogenin

The *E. coli* expression vector pHA1 containing a synthetic [Leu-30]angiogenin coding sequence under control of the trp promoter and containing an ampicillin marker was used. The leucine residue at position 30 was converted back to methionine as found in native angiogenin by oligonucleotide-directed mutagenesis by the method of Kunkel, Proc. Natl. Acad. Sci. USA 82: 488–492, 1985, employing the Muta-Gene TM mutagenesis kit. The amino acid sequence of the angiogenin encoded by this gene (pHA1) was identical to the sequence defined in U.S. Pat. No. 4,721,472, except that it codes for leucine (leu) at position 30 instead of methionine and contains methionine (met) at position -1 as shown in FIG. 5. The pHA2 expression vector was prepared as follows. pHA1 (4 µg) was digested with KpnI and PvuII followed by EcoRI and the KpnI/EcoRI fragment ligated into M13mp18 containing EcoRI and KpnI ends. After transformation into CaCl$_2$ treated JM101 cells (Maniatis et al., *Molecular Cloning, A Laboratory Manual*, Cold Spring Harbor Laboratory, 1983), recombinant plaques were identified by agarose gel electrophoresis. Phage (1.3×10$^7$ pfu) was used to infect a 20 ml culture of CJ236 (dut$^-$, ung$^-$) cells (Kunkel et al., *Methods in Enzymology* 154: 367–382, 1987) and the phage grown overnight at 37° C. Phage containing supernatants showed 2×10$^5$ difference in infectivity toward CJ236 and MV1190 (Kunkel et al., *Methods in Enzymology* 154: 367–382, 1987) cell lines. Uracil-containing M13mp18-HA1 single-stranded DNA was isolated by PEG/NaCl precipitation followed by phenol/chloroform extraction and 200 ng of this DNA annealed with the mutagenic primer pGAATCGATTATGAGACGCCG (2.7 pmol) in 20 mM Tris-HCl, pH 7.4 2 mM MgCl$_2$ and 50 mM NaCl. Second-strand synthesis was carried out using T4 DNA polymerase (1 U) and T4 DNA ligase (3U) in 23 mM Tris-HCl, pH 7.4, containing 1.5 mM DTT, 5 mM MgCl$_2$, 0.5 mM dNTP's and 0.75 mM ATP as described in the Muta-Gene manual. The double-stranded M13mp18-HA (10 ng) was used to transform MV1190 cells and plaques grown on agar plates overnight at 37° C. Sequencing of DNA obtained from 4 plaques identified three clones (M13mp18-HA2) which contained an ATG coding for Met at position 30. Double-stranded M13mp18-HA2 was digested with KpnI and EcoRI and the 428-bp fragment containing the angiogenin coding sequence purified by electrophoresis with 3.5% low melting agarose (NuSieve GTG, FMC BioProducts). After ligation into gel purified expression vector containing KpnI/EcoRI ends, the resulting pHA2 DNA was used to transform CaCl$_2$ treated JM101 cells.

Transformants were screened by restriction mapping of plasmid DNA. Individual colonies containing pHA2 were grown overnight in Luria broth (LB) containing 50 μg/ml ampicillin and cells were cryopreserved in 15% glycerol at −70° C. The preparation of pHA2 as just described is illustrated in FIG. 1. Plasmid pHA2 has been deposited with American Type Culture collected under accession number A.T.C.C. 67660. This new synthetic angiogenin gene in pHA2 codes for the same amino acid sequence as defined in U.S. Pat. No. 4,721,472, including Met-30 and Asp-116, but differs in that the expressed protein has a methionine at position minus one (Met−1) as shown in FIG. 5.

EXAMPLE 2

Mutagenesis of Asp-116 in Angiogenin

Figure 2:
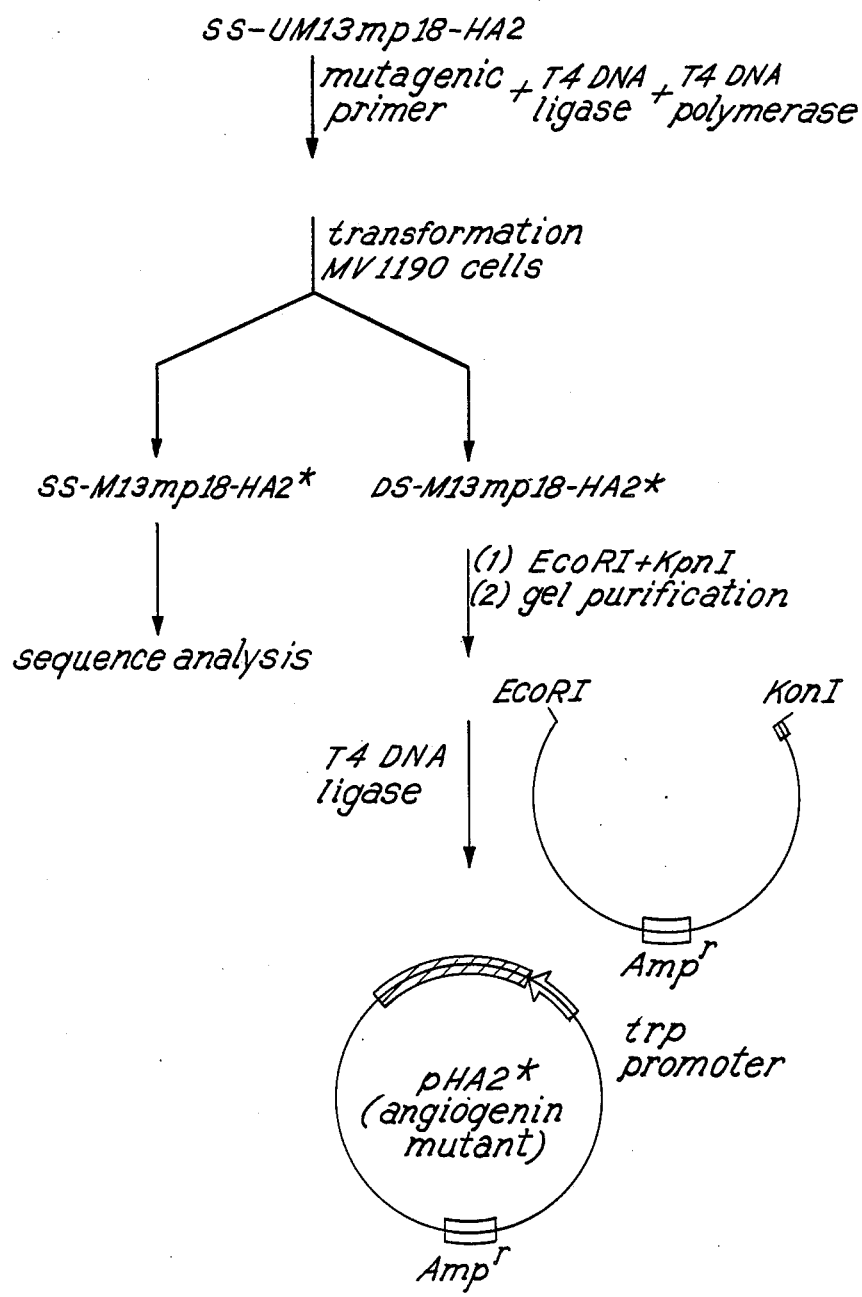
FIG. 2 illustrates the strategy used for mutagenesis of Asp-116 in angiogenin and construction of the expression vector for the mutant angiogenins.

Mutagenesis of Asp-116 in angiogenin was carried out by the oligonucleotide-directed mutagenesis method of Kunkel, Proc. Natl. Acad. Sci. USA 82: 488–492, 1985, using the Muta-Gene ™ in vitro mutagenesis kit. The preparation of mutant angiogenin genes is illustrated in FIG. 2 and is described as follows. The DNA and amino acid sequence of the wild-type angiogenin used for mutagenesis is shown in FIG. 5.

M13mp18-HA2 phage propagated in CJ236 cells (20 culture) and the uracil containing single-stranded DNA obtained by PEG/NaCl prepcipitation followed by phenol/chloroform extraction. This material showed $6 \times 10^5$ preference for infection of CJ236 cells compared with MV1190 cells. Single-stranded M13mp18-HA2 (880 ng, 0.44 pmol) was annealed with the synthetic oligonucleotide pGTCCATCTA(A/G/C)(C/A)(T/A)CAGT-CTATC (1.1 pmol) (which codes for a variety of mutations at the position of Asp-116 in angiogenin) in 20 mM Tris-HCl, pH 7.4, containing 2 mM $MgCl_2$ and 50 mM NaCl. Second strand synthesis and transformation of MV1190 cells was carried out as described above for M13mp18-HA2. Twenty-four plaques were selected and plaque purified. Mutant DNA's were identified by DNA sequencing using the chain termination method and employing the synthetic oligonucleotide which primes second-strand synthesis approximately 40 nucleotides 5' to the codon for Asp-116 in angiogenin. A total of 5 mutant DNA's were obtained: one coding for Asn-116 (codon=AAT), two coding for Ala-116 (codon=GCA), and two coding for His-116 (codon=CAT). The Asn-116 mutant is designated D116N-angiogenin; the Ala-116 mutant is designated D116A-angiogenin; and the His-116 mutant is designated D116H-angiogenin. The sequence of the entire coding region was determined in order to rule out the presence of any unintentional mutations. Double-stranded M13 DNA (1–2 μg) for each of these mutants was digested with KpnI and EcoRI, purified on 3.5% low-melting agarose gel electrophoresis (NuSieve GTG) and ligated into gel purified expression vector (25 ng) containing KpnI/EcoRI ends according to the FMC BioProducts protocol. Transformation of W3110 cells was accomplished using 2.5–10 ng of ligated plasmid. Eight colonies from each transformation were selected and carried through one cycle of replating. Individual colonies were grown overnight in LB with 50 μg/ml ampicillin and cells cryopreserved in 15% glycerol at −70° C. The preparation of mutant angiogenin DNAs is illustrated in FIG. 2.

Plasmid pHA2-D116N in W3110 cells containing the mutant gene for D116N-angiogenin has been deposited with American Type Culture Collection under accession number A.T.C.C. 67662; plasmid pHA2-D116A in W3110 cells containing the mutant gene for D116A-angiogenin has been deposited with American Type Culture Collection under accession number A.T.C.C. 67661; plasmid pHA2-D116H in W3110 cells containing the mutant gene for D116H-angiogenin has been deposited with American Type Culture Collection under accession number A.T.C.C. 67659.

EXAMPLE 3

Expression of Wild-type and Mutant Angiogenin

For large-scale expression, overnight cultures of W3110 cells harboring the appropriate expression plasmid were diluted 100-fold into 500 ml M9 media (Maniatis et al., *Molecular Cloning, A Laboratory Manual*, Cold Spring Harbor Laboratory, 1982) supplemented with 20 ml of 10% casamino acid (Difco), 10 ml of 20% glucose and 1 ml of ampicillin (25 mg/ml) and cells grown at 37° C. with vigorous shaking for 4 hours ($O.D._{600}$ of approximately 1.2). Indole-3-acrylic acid (0.5 ml, 20 mg/ml; Aldrich) and 10 ml of 20% glucose were added and the cells grown an additional 4 hours.

Cells from 6 to 8 colonies were initially examined for expression levels by immunoblotting analysis as follows. Cultures (10 ml) were grown as described above, cells from 1 ml of culture collected by centrifugation, and the cell pellet resuspended in 400 μl of sample buffer containing 0.2% SDS. DTT (150 μl, 0.2M) was added, and the mixtures heated at 100° C. for 3–5 minutes. Sodium dodecyl sulfate polyacrylamide gel electrophoresis (SDS-PAGE) was performed by using a 5% stacking gel and 15% separating gel. Gel slabs were washed twice in 25 mM Tris, 0.2M glycine, 20% methanol containing 0.1% SDS and proteins transferred to 0.45 μm nitrocellulose overnight at 27 V in the above Tris-glycine buffer. The nitrocellulose filter was washed with PBS/0.2% Tween-20 detergent (Tween) for two hours followed by a 2 hour incubation with affinity purified anti-angiogenin prepared as described in Example 5. The nitrocellulose filter was washed with PBS/Tween for 30 minutes then incubated with alkaline phosphatase labelled goat-antirabbit IgG (2.5 μg/ml, Kierkegaard and Perry Laboratories, Inc.) for 1.2 hours. After washing for 30 min with PBS/Tween, the blot was developed with nitroblue tetrazonium (0.1 mg/ml) and 5-bromo-4-chloro-3-indolyl-phosphate p-toluidine (0.5 mg/ml) in 0.1M barbital buffer (Sigma) containing 4 mM $MgCl_2$. Levels of expression were assessed by comparison with angiogenin standards.

Colonies which showed highest levels of expression were selected and grown in large-scale culture as described in Example 4 and the purified wild-type and mutant angiogenins (Example 4) further characterized in assays for ribonucleolytic activity and for angiogenic activity according to Examples 7 and 8, respectively.

EXAMPLE 4

Purification of Wild-type and Mutant Angiogenin

Cells from a 500-ml culture grown for expression of wild-type and mutant angiogenins as described in Example 3 were collected by centrifugation [5,500 rpm (GSA rotor), 10 minutes] and resuspended in 54 ml of 20 mM Tris-HCl (pH 7.4) containing 10% sucrose and 2.5 mM phenylmethane sulfonyl fluoride (PMSF). Lysozyme (3 ml, 2 mg/ml in Tris/sucrose buffer), NaCl (2.4 ml, 5M) and ethylenediamine tetraacetic acid (1.2 ml, 0.5M) were added and the mixture incubated for 45 min on an ice-water bath. PMSF (0.4 ml, 0.45M) was added and the mixture sonicated on ice through 3-7 cycles with 25 one-second pulses/cycle using a Branson Model 350 Sonifier, power setting 7. An addition 0.4 ml of PMSF (0.45M) was added at the end of the sonication period. The insoluble material was collected by centrifugation [12,000 rpm (SS34 rotor), 25 minutes], the pellet washed with 60-90 ml of Tris/sucrose buffer containing 2 mM PMSF and the pellet collected by centrifugation. The pellet was resuspended in 80 ml of water and the insoluble material collected by centrifugation [17,000 rpm (SS34 rotor), 30 minutes]. The pellet was dissolved in 5.0 ml of 7M guanidine-HCl, 100 mM potassium phosphate, pH 7.5 containing 0.1M $\beta$-mercaptoethanol and incubated at 37° C. for 3 hours. The mixture was added dropwise at 4° C. to 600 ml of 50 mM Tris-HCl, pH 8.5, containing 100 mM NaCl and 5 $\mu$g/ml lysozyme (as carrier) without stirring and allowed to stand for 20-25 hours. After stirring for 8-10 hours, 150 ml of NaCl (5M) was added, insoluble material removed by centrifugation [1100 rpm (GSA rotor), 30 minutes] and the crude angiogenin concentrated 100-fold by membrane ultrafiltration using an Amicon ultraconcentrator and a YM5 membrane. Six volumes of 10 mM Tris, pH 8.0, was added and then concentrated to 5-8 ml.

The crude angiogenin was then applied to a cation-exchange column (Mono-S, Pharmacia, Inc.) equilibrated with 10 mM Tris-HCl, pH 8.0, containing 0.15M NaCl and eluted with a linear gradient of NaCl (0.15M to 0.55M in 50 minutes). Shapiro et al., Biochemistry 26: 5141-5146 (1987). Peak fractions were then applied to a high pressure liquid chromatography (HPLC) column (Synchropak C18) and eluted with a linear gradient of solvents A and B (30-50% solvent B, 30 minutes, 0.8 ml/minute) where solvent A was 0.1% trifluoroacetic acid (TFA) and solvent B was 2-propanol:acetonitrile:water (3:2:2) containing 0.08% TFA. In some cases, peak fractions were rechromatographed on the same column prior to exhaustive dialysis against water. The concentration of purified protein was assessed by amino acid analysis as described by Bidlingmeyer et al., J. Chromatography 336: 93-104, (1984), using Picotag ™ methodology (Waters Associates). Final recovery of wild-type or mutant angiogenin ranged from 0.1-2.0 mg per liter of culture.

EXAMPLE 5

Preparation of Affinity-purified Rabbit Anti-Angiogenin

An affinity resin for anti-angiogenin antibodies was prepared as follows: recombinant angiogenin (1.25 mg) prepared as described by Vallee and Kurachi in U.S. Pat. No. 4,721,672, was dissolved in 2.5 ml of 0.1M NaHCO$_3$ (pH 9.0) and incubated with 0.5 g (2.5 ml) of cyanogen bromide (CNBr) activated agarose beads (CNBr-activated Sepharose 4B, Pharmacia) at 4° C. for 16 hours. The resin was washed sequentially with 100 ml each of 0.1M NaHCO$_3$, 2M NaCl and water. For purification of rabbit anti-angiogenin, anti-sera was obtained from rabbits injected with either plasma-derived angiogenin (Shapiro et al., Biochemistry 26: 5141-5146, 1987) or a recombinant angiogenin (U.S. Pat. No. 4,721,672). One milliliter of such antisera was diluted with 1 ml of PBS and applied to the resin equilibrated with PBS (flow rate=0.5 ml/min). Elution was monitored at 280 nm. After extensive washing with PBS (A$_{280}$ less than 0.01), antibodies were eluted with 3.5M MgCl$_2$ containing 10% dioxane followed by additional washing with PBS. The purified anti-angiogenin antibodies were used to test for expression of wild-type and mutant angiogenins by host cells as described in Example 3.

EXAMPLE 6

Characterization of Wild-type and Mutant Angiogenins

The amino acid compositions of purified wild-type and mutant angiogenins given in Table 1 are in excellent agreement with that expected based on the primary structure of angiogenin. These compositions are also consistent with the proposed mutations.

In order to insure that proper formation of the three disulfide bonds in angiogenin had occurred during renaturation of the reduced protein, tryptic peptide mapping was performed. Wild-type or mutant angiogenin (1-5 nmol) was incubated with HPLC purified trypsin (2-4%) in 10 mM Tris, pH 8.0, 0.35M NaCl overnight at 37° C. Peptides were purified by reverse-phase HPLC on an HPLC column (Ultrasphere C18) using linear gradients of 2-propanol/acetonitrile containing 0.1% TFA in water with a flow rate of 0.8 ml/minute Elution was monitored at 214 nm. Compositions of peptides were determined after acid hydrolysis using derivatization with phenylisothiocyanate and analysis by reverse-phase HPLC as described by Bidlingmeyer et al., J. Chromatography 336: 93-104 (1984), by the Picotag ™ methodology (Waters Associates).

TABLE 1

| Amino Acid | Amino Acid Composition of Wild-Type Angiogenin and Mutant Angiogenins | | | | | | | |
|---|---|---|---|---|---|---|---|---|
| | Wild-type angiogenin | | D116H-angiogenin | | D116A-angiogenin | | D116N-angiogenin | |
| Asp | 15.3 | (15) | 14.5 | (14) | 14.7 | (14) | 15.5 | (15) |
| Glu | 10.0 | (10) | 10.4 | (10) | 10.1 | (10) | 10.0 | (10) |
| Ser | 8.4 | (9) | 8.6 | (9) | 8.6 | (9) | 8.7 | (9) |
| Gly | 8.0 | (8) | 9.1 | (8) | 8.3 | (8) | 8.6 | (8) |
| His | 5.9 | (6) | 6.6 | (7) | 5.8 | (6) | 5.6 | (6) |
| Arg | 13.0 | (13) | 12.8 | (13) | 13.1 | (13) | 13.0 | (13) |
| Thr | 6.7 | (7) | 6.8 | (7) | 7.0 | (7) | 7.1 | (7) |
| Ala | 5.1 | (5) | 5.3 | (5) | 6.2 | (6) | 5.3 | (5) |
| Pro | 8.1 | (8) | 7.8 | (8) | 8.0 | (8) | 7.9 | (8) |
| Tyr | 3.9 | (4) | 3.9 | (4) | 3.9 | (4) | 3.8 | (4) |
| Val | 4.1 | (5) | 4.3 | (5) | 4.2 | (5) | 4.4 | (5) |
| Met | 2.1 | (2) | 2.1 | (2) | 2.1 | (2) | 2.1 | (2) |
| Ile | 6.5 | (7) | 6.6 | (7) | 6.7 | (7) | 6.9 | (7) |
| Leu | 5.9 | (6) | 6.1 | (6) | 5.9 | (6) | 5.9 | (6) |
| Phe | 4.9 | (5) | 4.9 | (5) | 5.0 | (5) | 5.0 | (5) |
| Lys | 7.0 | (7) | 7.1 | (7) | 7.3 | (7) | 7.3 | (7) |
| pmol analyzed | 250 | | 122 | | 110 | | 96 | |

The tryptic peptide maps of each mutant angiogenin were virtually indistinguishable from the maps of wild-type angiogenin. In particular, all three disulfide bonded peptides (T-9, T-10 and T-11) are present in all digests, indicating proper folding. The composition of some of the tryptic peptides obtained in pure form are shown in Tables 2 3, and 4. FIG. 4 shows the position of each tryptic peptide in the DNA and amino acid sequence of the angiogenin gene used for mutagenesis.

TABLE 2

Amino Acid Composition of some Tryptic Peptides from Recombinant D116H-Angiogenin[a]

| peptide: | T-2 | | T-5 | | T-7 | | T-8,[b] T-9 | | T-11 | |
|---|---|---|---|---|---|---|---|---|---|---|
| Asp | 0.35 | | 1.17 | (1) | 1.24 | (1) | 4.60 | (5) | 3.04 | (3) |
| Glu | 0.49 | | 1.28 | (1) | 2.13 | (2) | 2.10 | (2) | 3.37 | (3) |
| Ser | 0.59 | | 0.72 | | 0.48 | | 3.08 | (3) | 2.53 | (1) |
| Gly | 1.05 | | 1.24 | | 1.52 | (1) | 2.04 | (1) | 3.74 | (1) |
| His | 0.18 | | 0.21 | | 1.75 | (2) | 1.31 | (1) | 1.65 | (2) |
| Arg | 1.04 | (1) | 0.98 | (1) | 1.02 | (1) | 2.51 | (3) | 1.33 | (1) |
| Thr | 0.24 | | 0.25 | | 1.83 | (2) | 2.80 | (3) | 0.87 | |
| Ala | 0.21 | | 0.24 | | 1.15 | (1) | 0.36 | | 1.95 | (2) |
| Pro | 1.00 | (1) | | | 1.01 | (1) | 0.23 | | 1.29 | (1) |
| Tyr | 0.19 | | 0.15 | | 1.67 | (2) | 0.94 | (1) | 0.61 | |
| Val | 0.24 | | 0.17 | | 0.19 | | 1.07 | (1) | 2.64 | (4) |
| Met | 0.28 | | 0.19 | | 0.19 | | 1.17 | (1) | | |
| Ile | 0.16 | | 0.15 | | 0.16 | | 2.65 | (3) | 1.79 | (2) |
| Leu | 0.27 | | 0.96 | (1) | 1.06 | (1) | 0.36 | | 2.09 | (2) |
| Phe | 0.17 | | 0.17 | | 0.96 | (1) | 1.88 | (2) | 1.14 | (1) |
| Lys | 0.31 | | 0.36 | | 1.22 | (1) | 2.18 | (2) | 1.50 | (1) |
| pmol analyzed | 105 | | 100 | | 95 | | 35 | | 53 | |
| sequence position | 122–123 | | 67–70 | | 6–21 | | 41–51, 22–31 + 74–84 | | 55–60 + 102–121 | |

[a]Relative molar amounts of amino acids are given. Analyses are not corrected for Gly, Ser, Ala and Asp which are present at this level in some of the HPLC fractions. The number in parenthesis indicates the number of residues expected based on the sequence. Quantities less than 0.10 equivalents are not indicated.
[b]Peptides T-8 and T-9 comigrate in this separation system. Thus, the composition given is the composite of both peptides.

TABLE 3

Amino Acid Composition of Tryptic Peptides from D116N-Angiogenin[a]

| peptide: | T-1 | | T-2 | | T-3a[b] | | T-3b | | T-4a[c] | |
|---|---|---|---|---|---|---|---|---|---|---|
| Asp | 2.66 | (2) | 0.21 | | 0.80 | | 0.59 | | 2.0 | (2) |
| Glu | 1.06 | (1) | 0.31 | | | | 0.43 | | 0.31 | |
| Ser | 1.28 | (1) | 0.36 | | 0.98 | (1) | 1.31 | (1) | 0.46 | |
| Gly | 0.43 | | 0.64 | | 0.51 | | 0.20 | | 2.25 | (1) |
| His | 0.31 | | | | 0.45 | | | | 1.09 | (1) |
| Arg | 1.30 | (1) | 1.04 | (1) | 0.43 | | 0.32 | | 4.61 | (1) |
| Thr | 0.11 | | 0.18 | | 0.13 | | 0.13 | | 1.15 | |
| Ala | | | 0.13 | | | | | | 0.26 | |
| Pro | 0.28 | | 0.99 | (1) | 0.42 | | 0.13 | | 4.55 | (1) |
| Tyr | | | | | | | | | 0.17 | |
| Val | | | | | | | | | 0.18 | |
| Met | 1.00 | (1) | | | | | 0.28 | | 0.58 | |
| Ile | 0.31 | | | | 0.99 | (1) | 1.00 | (1) | 0.15 | |
| Leu | | | 0.16 | | | | | | 0.21 | |
| Phe | | | | | | | | | | |
| Lys | 0.35 | | 0.17 | | 1.05 | (1) | 1.00 | (1) | 0.47 | |
| pmol analyzed | 300 | | 270 | | 270 | | 280 | | 30 | |

| peptide: | T-6 | | T-7 | | T-8 | | T-9 | | T-11 | |
|---|---|---|---|---|---|---|---|---|---|---|
| Asp | 0.46 | | 1.14 | (1) | 2.80 | (3) | 2.27 | (2) | 4.38 | (4) |
| Glu | 0.18 | | 2.14 | (2) | | | 2.06 | (2) | 3.02 | (3) |
| Ser | | | 0.14 | | 0.11 | | 3.11 | (3) | 1.22 | (1) |
| Gly | 1.34 | (1) | 1.37 | (1) | 1.82 | (1) | 0.49 | | 2.00 | (1) |
| His | 0.19 | | 2.04 | (2) | 0.98 | (1) | 0.13 | | 1.15 | (1) |
| Arg | 1.28 | (1) | 1.12 | (1) | 0.97 | (1) | 2.18 | (2) | 1.34 | (1) |
| Thr | 1.09 | (1) | 2.04 | (2) | 1.06 | (1) | 2.22 | (2) | 0.37 | |
| Ala | 2.08 | (2) | 1.08 | (1) | 0.12 | | | | 1.91 | (2) |
| Pro | 0.18 | | 1.09 | (1) | | | | | 1.56 | (1) |
| Tyr | | | 1.97 | (2) | | | 1.00 | (1) | 0.11 | |
| Val | | | | | | | 0.98 | (1) | 2.72 | (4) |
| Met | | | 0.14 | | 0.20 | | 1.09 | (1) | 0.19 | |
| Ile | 0.16 | | | | 1.64 | (2) | 1.07 | (1) | 1.86 | (2) |
| Leu | | | 1.00 | (1) | 0.15 | | | | 2.13 | (2) |
| Phe | 0.99 | (1) | 1.00 | (1) | 0.84 | (1) | 1.03 | (1) | 1.00 | (1) |
| Lys | 0.07 | | 1.07 | (1) | 1.00 | (1) | 1.14 | (1) | 1.27 | (1) |
| pmol analyzed | 240 | | 263 | | 90 | | 150 | | 143 | |

TABLE 3-continued

Amino Acid Composition of Tryptic Peptides from D116N-Angiogenin[a]

[a]Relative molar amounts of amino acids are given. Peptides are designated as described earlier (Strydom et al., Biochemistry 24: 5486–5494, 1985) and as shown in FIG. 4. Analyses are not corrected for Gly, Ser, Ala and Asp which are present at this level in some of the HPLC fractions. The number in parenthesis indicates the number of residues expected based on the sequence. Quantities less than 0.10 equivalents are not indicated.
[b]Contains 40 pmole of T-4a.
[c]Contains 100 pmole of T-2.

TABLE 4

Amino Acid Compositions of Tryptic Peptides from D116A-Angiogenin[a]

| peptide: | T-1 | | T-2 | | T-3a[b] | | T-3b | | T-4a | |
|---|---|---|---|---|---|---|---|---|---|---|
| Asp | 2.10 | (2) | | | 1.50 | | 0.62 | | 1.44 | (2) |
| Glu | 0.92 | (1) | | | 0.42 | | 0.34 | | 0.23 | |
| Ser | 1.38 | (1) | 0.11 | | 1.26 | (1) | 1.39 | (1) | 0.32 | |
| Gly | 0.45 | | 0.43 | | 1.00 | | 0.62 | | 1.27 | (1) |
| His | 0.19 | | | | 0.51 | | 0.14 | | 0.66 | (1) |
| Arg | 1.02 | (1) | 0.97 | (1) | 0.74 | | 0.31 | | 1.13 | (1) |
| Thr | | | | | | | | | | |
| Ala | | | | | | | | | | |
| Pro | 0.20 | | 1.00 | (1) | 0.55 | | | | 1.16 | (1) |
| Tyr | | | | | | | | | | |
| Val | | | | | | | | | | |
| Met | 0.75 | (1) | | | 0.18 | | 0.25 | | | |
| Ile | 0.59 | | | | 1.07 | (1) | 1.07 | (1) | 0.16 | |
| Leu | | | | | 0.13 | | | | 0.11 | |
| Phe | | | | | | | | | | |
| Lys | 0.46 | | | | 0.87 | (1) | 0.82 | (1) | 0.24 | |
| pmol analyzed | 200 | | 270 | | 180 | | 95 | | 75 | |

| peptide: | T-5 | | T-6 | | T-11 | | | |
|---|---|---|---|---|---|---|---|---|
| Asp | 1.16 | (1) | 0.36 | | 3.00 | | (3) | |
| Glu | 1.25 | (1) | 0.26 | | 3.27 | | (3) | |
| Ser | 0.46 | | 0.23 | | 1.95 | | (1) | |
| Gly | 0.96 | | 1.68 | (1) | 3.48 | | (1) | |
| His | | | 0.17 | | 0.82 | | (1) | |
| Arg | 0.97 | (1) | 1.17 | (1) | 1.38 | | (1) | |
| Thr | 0.12 | | 0.95 | (1) | 0.65 | | | |
| Ala | 0.15 | | 2.01 | (2) | 2.70 | | (3) | |
| Pro | 1.16 | (1) | 0.15 | | 1.43 | | (1) | |
| Tyr | 0.12 | | | | 0.24 | | | |
| Val | 0.13 | | | | 2.56 | | (4) | |
| Met | | | | | | | | |
| Ile | 0.13 | | | | 1.55 | | (2) | |

| peptide: | T-5 | | T-6 | | T-11 | | | |
|---|---|---|---|---|---|---|---|---|
| Leu | 1.00 | (1) | 0.18 | | 2.36 | | (2) | |
| Phe | 0.11 | | 1.00 | (1) | 1.02 | | (1) | |
| Lys | 0.14 | | 0.15 | | 0.90 | | (1) | |
| pmol analyzed | 180 | | 130 | | 90 | | | |

[a]Relative molar amounts of amino acids are given. Peptides are designated as described earlier (Strydom et al., Biochemistry 24: 5486–5494, 1985) and as shown in FIG. 4. Analyses are not corrected for Gly, Ser, Ala and Asp which are present at this level in some of the HPLC fractions. The number in parenthesis indicates the number of residues expected based on the sequence. Quantities less than 0.10 equivalents are not indicated.
[b]Contains 100 pmol of T-4a, which contributes substantially to the levels of Asp, Glu and Arg in this analysis.

As shown in Tables 2, 3 and 4 the compositions of peptide T-11 (T-11' and T-11") from the mutant angiogenin proteins are consistent with the desired mutations. No other alterations in structure were evident. Peptide T-10, which exists as two interconvertible forms due to the presence of a cis-trans proline residue, was observed in all digests. [Note that peptide T-11 is composed of peptide T-11' (residues 55–60) which is disulfide bonded to peptide T-11" (residues 102–121); also, peptide T-9 is composed of peptide T-9' (residues 22–31) which is disulfide bonded to peptide T-9" (residues 74–82); further, peptide T-10 is composed of peptide T-10' (residues 34–40) which is disulfide bonded to T-10" (residues 83–95)]. These peptides are shown in FIG. 4.

EXAMPLE 7

Enzymatic Assays

Activity towards tRNA was determined using the precipitation assay described by Shapiro et al., Proc. Natl. Acad. Sci. USA 84: 8783–8787 (1987). Reaction mixtures containing 33 mM Hepes, pH 7.0, 33 mM NaCl, 0.6 mg of tRNA (Sigma type X) and 30 μg of human serum albumin, in a volume of 300 μl were incubated at 37° C. for 2.5–4 hours. The reaction was terminated by addition of 700 μl of ice-cold 3.4% perchloric acid, and after 10 minutes on ice the samples were centrifuged at 15600 g for 10 minutes at 4° C. The absorbance of the supernatant at 260 nm was then measured.

Activity towards rRNA (18S and 28S) was assessed by gel electrophoresis (Shapiro et al., Biochemistry 25: 3527–3532, 1986).

Activity toward the RNase substrates cytidyl (3'→5') adenosine (CpA) and uridyl (3'→5') adenosine (UpA) was determined using a sensitive HPLC method described previously (Shapiro et al., Biochemistry 25: 3527–3532 and 7255–7264 1986). Reaction mixture containing 30 mM 2-(N-morpholino) ethane sulfonic acid (Mes), pH 6.0, 30 mM NaCl and 0.1 mM dinucleoside phosphate were incubated with angiogenin (0.7–3.0 μM) at 37° C. Aliquots (15–20 μl) were removed at various times and injected onto an HPLC column (radial Pak C18; Waters Associates) equilibrated with 10 mM potassium phosphate, pH 7.0. Elution of reactants and products was accomplished using a linear gradient of methanol in 100 mM potassium phosphate pH 7.0 at a flow rate of 0.8 ml/minutes. Elution was monitored at 254 nm and the integrated areas of reactants and products used to calculate $k_{cat}/K_m$ using the expression $k_{cat}/K_m = \ln \{[S]_o/[S]_t\}/[E]t$.

Alterations in ribonucleolytic activity of Asp-116 mutants of angiogenin were initially examined using tRNA as substrate at pH 7.0 as stated above. The results are shown in FIG. 3 (A and B). FIG. 3A shows the change in absorbance at 260 nm ($\Delta A_{260}$) as a function of mutant or wild type angiogenin protein concentration (0–10 μg/ml). FIG. 3B simply shows an expanded version of a portion of FIG. 3A for the concentrations between 0 and 1.2 μg/ml. D116H-angiogenin (shown with closed squares in FIG. 3 and labelled as His-116) and D116A-angiogenin (shown with open squares in FIG. 3 and labelled as Ala-116) are 15 fold more active than wild-type angiogenin (shown with closed circles in FIG. 3 and labelled as wild-type, Asp-116), while D116N-angiogenin (shown with open circles in FIG. 3 and labelled as Asn-116) is 8 fold more active than wild-type. In this assay, significant curvature is observed with wild-type angiogenin, which apparently reflects the limited number of cleavable sites in tRNA. Comparison of the relative enzymatic activities of wild-type and mutant angiogenins along the curve indicates an identical degree of curvature for wild-type and mutant angiogenins. In contrast, when pancreatic RNase is used in the assay, there is no similar curvature and the $\Delta A_{260}$ over the range is linear.

The pH profile for cleavage of tRNA was examined with the angiogenin mutants as well as the wild-type enzyme. Optimal activity was observed at approximately pH 7.0. From pH 5 to 10, the shapes of the pH profile for the mutants were virtually indistinguishable from those of wild-type angiogenin, except for D116A-angiogenin. In this case, the pH optimum was similar but somewhat higher activity was observed from pH 6.0–6.8 when compared to the wild-type enzyme.

The activity of D116H-angiogenin was also assessed with rRNA (18S and 28S) at pH 7.0 as described by Shapiro et al., Biochemistry 25: 3527–3532 (1986). At 15 fold lower concentrations of mutant angiogenin, the time course for formation of the characteristic polynucleotide products generated by wild-type angiogenin is closely similar. Thus, a 12 to 15 fold enhancement of ribonucleolytic activity was observed, consistent with the results in the tRNA assay.

The activity of the mutant angiogenin proteins toward the conventional RNase substrates CpA and UpA has been determined and is compared with the activity of wild-type angiogenin in Table 5. In contrast to the marked enhancement observed with both tRNA and rRNA as substrates, a 3.3- and 1.3-fold enhancement is observed with CpA as substrate for D116H-angiogenin and D116A-angiogenin, respectively. D116N-angiogenin is about 45% less active than wild-type angiogenin. Activities towards UpA are at least an order of magnitude lower, and again, only minor differences are noted among wild-type and mutant angiogenin proteins. For comparison, the $k_{cat}/K_m$ values of bovine RNase A with CpA and UpA are $6 \times 10^6 M^{-1} s^{-1}$ and $4 \times 10^6 M^{-1} s^{-1}$, respectively, when measured under conditions employed here [Harper et al., Biochemistry 27: 219–226 (1987)]. Thus, a novel feature of these mutations is a dramatic increase in the ribonucleolytic activity characteristic of angiogenin without a marked alteration in activity toward conventional RNase substrates, such as CpA and UpA.

TABLE 5

| | Cleavage of dinucleoside phosphates by angiogenin and Asp-116 angiogenin mutants | | | |
|---|---|---|---|---|
| | $k_{cat}/K_m$ (M$^{-1}$s$^{-1}$) | | | |
| Substrate | Wild-type angiogenin | D116A-angiogenin | D116H-angiogenin | D116N-angiogenin |
| CpA | 12 | 16 | 40 | 7 |
| UpA | 0.5 | 0.9 | 2.9 | 0.5 |

EXAMPLE 8

Biological Assays

Angiogenic activity was assessed using the chick embryo chorioallantoic membrane (CAM) assay method of Knighton et al., Br. J. Cancer 35: 347–356 (1977) as described by Fett et al., Biochemistry 24: 5480–5486 (1985). The number of eggs employed in any individual set of assays for a given concentration ranged from 10–15.

CAM activity data as shown in Table 6 from D116H-angiogenin was collected from 8 separate experiments along with activity data obtained concurrently in each experiment using the wild-type angiogenin. The data indicate a 10 to 100 fold increase in angiogenic potency by mutation of Asp-116 to His-116. For example, at 0.05 ng the mutant angiogenin protein shows maximal activity (i.e., approaching 60% positive response), while the activity of wild-type angiogenin has decreased substantially. Even at 1 picogram, D116H-angiogenin shows significant activity in the assay. Because the angiogenic activity and ribonucleolytic activity have correlated for all angiogenin proteins studied thus far, and because each of the mutant angiogenin proteins has exhibited significantly enhanced ribonucleolytic activity, it is expected that D116A-angiogenin and D116N-angiogenin would exhibit angiogenic activity similar to D116H-angiogenin, substantially enhanced over the wild-type activity.

TABLE 6

Angiogenic Activity of D116H and Wild-Type Angiogenin

| Sample | Dose (ng) | % positive (total number of eggs) |
|---|---|---|
| D116H-angiogenin | 20 | 59 (22) |
| | 10 | 53 (26) |
| | 5 | 44 (48) |
| | 1 | 56 (34) |
| | 0.5 | 58 (36) |
| | 0.05 | 45 (40) |
| | 0.005 | 42 (35) |
| | 0.001 | 36 (11) |
| wild-type angiogenin | 10 | 60 (47) |
| | 5 | 51 (70) |
| | 1 | 52 (50) |
| | 0.5 | 33 (24) |
| | 0.05 | 24 (25) |
| | 0.005 | 27 (11) |
| $H_2O$ | | 14 (69) |

EXAMPLE 9

Removal of Met (−1) from wild-type or mutant angiogenin expressed in *E. coli*.

Wild-type or mutant angiogenin obtained by expression in *E. coli* differs from plasma angiogenin in that the former contains an N-terminal methionine [Met (−1)] while the latter contains a pyroglutamic acid (cyclized glutamine). The ribonucleolytic and angiogenic activity of *E. coli*-derived wild-type angiogenin (containing an N-terminal methionine) is indistinguishable from that of plasma derived angiogenin (Shapiro et al., Biochemistry 25: 3527–3532, 1987) and that of the angiogenin expressed in baby hamster kidney (BHK) cells (U.S. Pat. No. 4,721,672).

Nevertheless, for some applications it may be advantageous to remove the N-terminal methionine in a manner which would provide angiogenin with N-terminal pyroglutamic acid. This has been accomplished as follows. Treatment of Met (−1) angiogenin (5–7 μM) with 1 nM Aeromonas aminopeptidase in 200 mM potassium phosphate pH 7.2, at 37° C. for 24 hours resulted in greater than 95% removal of Met(−1) with spontaneous and quantitative cyclization of glutamine (Gln-1) to pyroglutamic acid. These results were based on N-terminal sequencing and amino acid analysis of reverse-phase HPLC purified wild-type angiogenin after treatment with the peptidase. This material showed activity equivalent to that of plasma or BHK cell derived material. Similar treatment of a mutant angiogenin will act to remove Met (−1) to yield N-terminal pyroglutamic acid.

From the foregoing, it will be appreciated that although specific embodiments of the invention have been described herein for purposes of illustration, various modifications may be made without deviating from the spirit and scope of the invention. Accordingly, the invention is not limited except as by the appended claims.

What is claimed is:

1. A mutant angiogenin protein wherein the aspartic acid at position 116 as shown in FIG. 5 has been replaced with another amino acid, the mutant angiogenin protein having increased angiogenic and ribonucleolytic activity.

2. A mutant angiogenin protein according to claim 1 wherein the amino acid replacing the aspartic acid at position 116 with asparagine, alanine or histidine.

3. An isolated DNA sequence comprising a coding sequence for the mutant angiogenin protein of claim 1.

4. An isolated DNA sequence comprising a coding sequence for the mutant angiogenin protein of claim 2.

5. A vector capable of transforming a bacterial host cell comprising the DNA sequence of claim 3.

6. A vector according to claim 5 further comprising a tryptophan promoter and a translation initiation region sequence operably linked to said DNA sequence.

7. A vector capable of transforming a bacterial host cell comprising the DNA sequence of claim 4.

8. A vector according to claim 7 further comprising a tryptophan promoter and a translation initiation region sequence operably linked to said DNA sequence.

9. A host cell transformed or transfected to contain and express a DNA sequence coding for the protein of claim 1.

* * * * *